(12) United States Patent
Walker

(10) Patent No.: US 8,515,782 B2
(45) Date of Patent: Aug. 20, 2013

(54) PROCESSING MEDICAL RECORDS

(76) Inventor: Everett Darryl Walker, Smyrna, GA (US)

( * ) Notice: Subject to any disclaimer, the term of this patent is extended or adjusted under 35 U.S.C. 154(b) by 0 days.

(21) Appl. No.: 13/045,352

(22) Filed: Mar. 10, 2011

(65) Prior Publication Data
US 2012/0233215 A1    Sep. 13, 2012

(51) Int. Cl.
*G06Q 50/00* (2012.01)
*G06Q 10/00* (2012.01)

(52) U.S. Cl.
USPC .................................. 705/3; 705/2

(58) Field of Classification Search
USPC .................................................. 705/3
See application file for complete search history.

(56) References Cited

U.S. PATENT DOCUMENTS

| | | | |
|---|---|---|---|
| 5,319,543 A | 6/1994 | Wilhelm | |
| 5,664,109 A * | 9/1997 | Johnson et al. | 705/3 |
| 6,088,695 A | 7/2000 | Kara | |
| 6,235,176 B1 | 5/2001 | Schoen et al. | |
| 6,324,516 B1 | 11/2001 | Shults et al. | |
| 7,302,398 B2 | 11/2007 | Ban et al. | |
| 7,508,537 B2 | 3/2009 | Treibach-Heck et al. | |
| 2002/0038226 A1 | 3/2002 | Tyus | |
| 2003/0167184 A1 | 9/2003 | Kole | |
| 2003/0167189 A1 * | 9/2003 | Lutgen et al. | 705/3 |
| 2007/0219829 A1 | 9/2007 | Kay | |
| 2008/0033754 A1 * | 2/2008 | Smith et al. | 705/2 |
| 2011/0082710 A1 * | 4/2011 | Subash et al. | 705/3 |

OTHER PUBLICATIONS

Neamatullah, Automated de-identification of free-text medical records, Jul. 24, 2008, BMC Medical Informatics and Decision Making, vol. 8, No. 32.*
International Search Report and Written Opinion mailed Nov. 8, 2012 in Application No. PCT/US12/27965, 13 pages.

* cited by examiner

*Primary Examiner* — Tran Nguyen
(74) *Attorney, Agent, or Firm* — Merchant & Gould

(57) ABSTRACT

Processing medical records may be provided. First, medical records may be received from a plurality of sources. The medical records may then be converted into a computer-readable form. Once converted, the medical records may be searched for certain key words, phrases, or symbols. These searched key words, phrases and symbols may correspond to data of interest within the medical records. Once located, the searched key words, phrases and symbols may be extracted from the medical records, as well as an area of the records surrounding the located key words, phrases and symbols. Finally, the extracted data may be used to generate a summary report.

16 Claims, 5 Drawing Sheets

_140_

```
Summary Report # 1
History of Present Illness//Subjective Data

4/20/05
Subjective: Mr. Doe comes to the office complaining of persistent cough over past 10
days. He reports production of green sputum on occasion for last 3 days with episodes
of fever and chills starting yesterday. He has no history of pneumonia but is a smoker
with a 25+ pack year history.   Page 78

5/2/06                                                   510
History of Present Illness:
This is a 55 year-old male who presents with a one day history of back pain at the
lower spine. He sates that he lifted some equipment at work weighing approximately
70 lbs over a 10 minute period. The patient recalls experiencing…..   Page 225
```
                                                                                    _520_

*FIG. 5*

PROCESSING MEDICAL RECORDS

BACKGROUND

When an individual applies for disability benefits with his disability insurer, the insurer must obtain the individual's medical records from a variety of medical record sources to determine whether to allow a claim for disability benefits. Medical record may be obtained from physician offices, hospitals, physical therapy facilities, and other health care providers.

When the insurer receives the individual's medical records, the insurer places the records in a file (paper or electronic) in the order in which the records are received from the various medical sources. A case manager attempts to organize the file in a manner that helps the insurer determine whether to allow a claim. The task of organizing these medical records can be laborious and time-consuming. Medical records for a particular case may range from as few as fifty pages to more than a thousand pages. An average number of pages is between 100 and 300 pages.

Accordingly, there is a need for efficient organization and review of medical records to help disability insurers determine whether to allow a claim.

SUMMARY

Processing medical records may be provided. First, medical records may be received from a plurality of sources. The medical records may then be converted into a computer-readable form. Once converted, the medical records may be searched for certain key words, phrases, or symbols. These searched key words, phrases and symbols may correspond to data of interest within the medical records. Once located, the searched key words, phrases and symbols may be extracted from the medical records, as well as an area of the records surrounding the located key words, phrases and symbols. Finally, the extracted data may be used to generate a summary report.

It is to be understood that both the foregoing general description and the following detailed description are examples and explanatory only, and should not be considered too restrictive in scope, as described and claimed. Further, features and/or variations may be provided in addition to those set forth herein. For example, various embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments. In the drawings:

FIG. 5 is a diagram of an illustrative summary report, in accordance with an embodiment.

DETAILED DESCRIPTION

Figure 1:
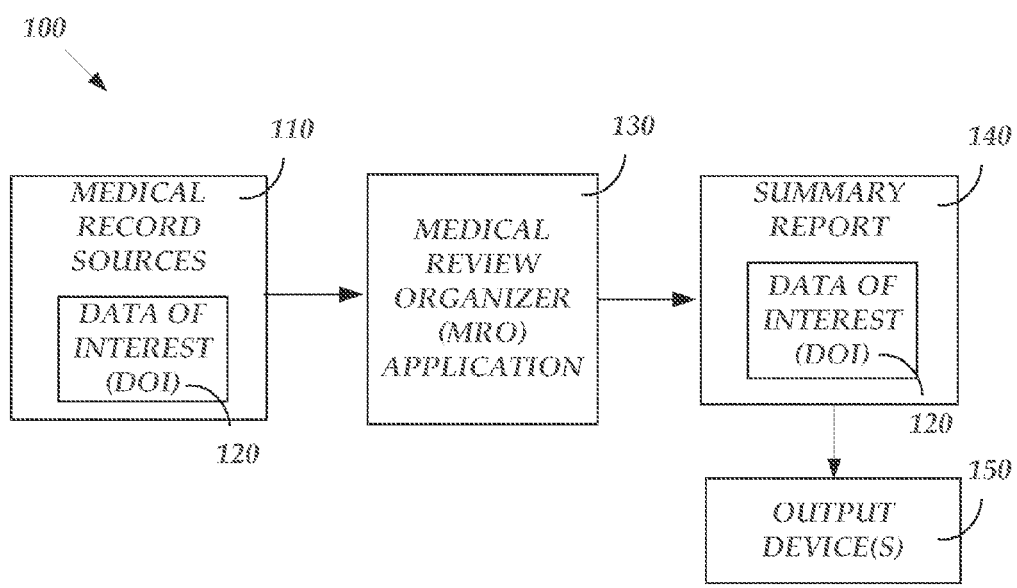
FIG. 1 is a block diagram of an operating environment for processing medical records, in accordance with various embodiments.

The following detailed description refers to the accompanying drawings. Wherever possible, the same reference numbers are used in the drawings and the following description to refer to the same or similar elements. While embodiments may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the embodiments. Instead, the proper scope is defined by the appended claims.

To determine whether a claimant is eligible for disability benefits, personnel whom review medical records for the insurer ("reviewers") may need to understand the course of a disease (or diseases) in question to determine, for example, the validity of a claimed illness, its severity, and potential long-term prognosis, among other things. Generally, the determination regarding eligibility for disability benefits may be based on a predetermined set of criteria.

To facilitate the medical record analysis, embodiments may efficiently organize medical records received from multiple sources, extract data of interest from these records, and provide a report that may summarize the data of interest to a reviewing party to facilitate the analysis process. FIG. 1 illustrates an operating environment 100 consistent with various embodiments. Environment 100 may comprise one or more medical record sources 110 having data of interest (DOI) 120, a medical review organizer (MRO) 130, a summary report 140, and one or more output devices 150.

Medical records may originate from numerous sources 110. Sources 110 may comprise physician offices, hospitals, physical therapy facilities, diagnostic testing facilities, other health care providers, patients, or any other source. The medical records may include DOI 120, among other things, which may be comprised of typewritten or printed text.

As discussed above, when an individual applies for disability benefits with his disability insurer, the insurer may need to obtain the individual's medical records from a variety of medical record sources. Upon receiving a medical record from, for example, an individual healthcare provider, the specific medical record may be placed in a database created for the particular claimant. Additional medical records are collected and added into this same database that may be given an identifier that is linked to the name of the claimant. Once all medical records have been received for the claimant, the completed database typically may contain from one to more than 20 sets of medical records from various sources 110 (e.g., doctor's offices, emergency rooms, hospitals, and rehabilitation centers). The collected body of medical data may be organized based on the date of receipt (i.e., based on the date the actual medical record is received by the reviewer). However, the medical records may be organized only by the source providing the specific medical record and the date of receipt. Generally, there is no regard given to the time frame of the actual claimant/patient visit to the healthcare sources resulting in a chronologically disorganized array of medical information. Appendix D illustrates a sample collection of medical records that may be received from sources 110.

In various embodiments, medical records may be received from sources 110 in a variety of ways including, but not limited to, electronically via a communication link, as a hard copy via mail or in person, on a storage device, or a combination of the foregoing. The communication link may be any system, network, or device that facilitates communication using any appropriate communication protocol. In this way, the medical records may be provided directly to MRO application 130 from sources 110 or may be inputted manually to MRO application 130 once received by a reviewing party via, for example, a scanning device.

Once the medical records are received at MRO application 130, MRO application 130 may process the records. Accordingly, MRO application 130 may comprise, or work in operation with, a processing unit and memory storage device to execute computer instructions for processing the records. Thus, MRO application 130 may comprise, for example, hardware and/or software elements operative to, among other actions, receive, store, read, search, parse, extract, organize, or otherwise process the medical records to provide summary reports. Furthermore, as will be discussed in greater detail with reference to FIG. 3, MRO application 130's processing and generation of summary reports 140 associated with the medical records may be customized by a user.

In various embodiments, the output of the MRO application 130, such as a generated summary report 140, may be transmitted to any output device 150 (such as a printer or display device) for a reviewer to view the output to make a determination on a particular claim. In addition, the generated summary report may be electronically communicated to a reviewing party via, for example, email or other forms of electronic communication between systems and/or networks.

Figure 2:
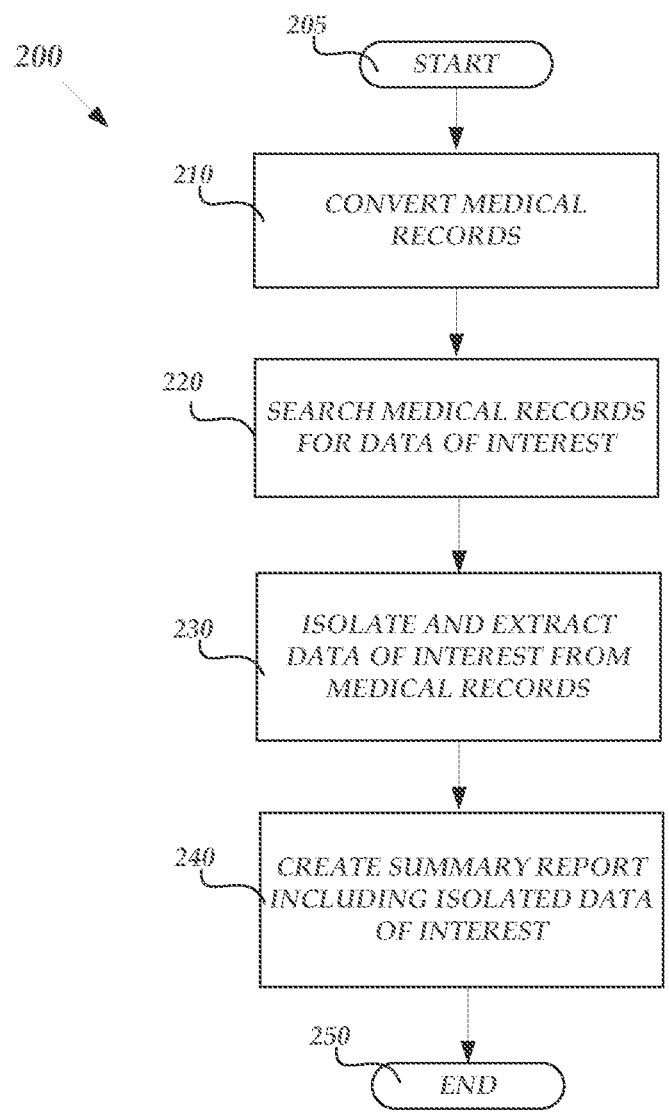
FIG. 2 is a flow chart of a method for processing medical records, in accordance with various embodiments.

FIG. 2 is a flow chart setting forth the general stages involved in a method 200 consistent with various embodiments for extracting DOI 120 to facilitate the analysis process. Method 200 may be implemented using a computing device. An illustrative computing device may include computing device 400 of FIG. 4 (which will described in greater detail below). An illustrative implementation of the stages of method 200 will now be described.

Method 200 may begin at starting block 205 and proceed to stage 210 where computing device 400 may convert the received medical records, or a subset thereof, into a computer readable and searchable form. For example, to properly process the received medical records, MRO application 130 may first need to read and parse through the medical records. Accordingly, MRO application 130 may include, and/or operate in conjunction with, optical character recognition functionality or other character recognition functionality to convert medical records into computer readable/searchable form. In accordance with some embodiments, however, MRO application 130 may have received the electronic documents in a computer readable/searchable form not requiring conversion.

From stage 210, where computing device 400 converts the medical records, method 200 may advance to stage 220 where computing device 400 may search through the medical records for the DOI 120. For example, MRO application 130 may comprise searching functionality operative to search through the converted medical records. The searching functionality may be used to, for example, identify documents containing key words, phrases, and/or symbols. The key words, phrases, and symbols may be manually specified by a user of MRO application 130 or, in various embodiments, may be programmed into MRO application 130 as default search parameters or user-selected search parameters from a menu of a predetermined list of key words, phrases, and symbols.

Preferably, the keywords, phrases, and symbols are chosen so that the MRO application 130 can identify documents or portions of documents containing the information needed to make a determination regarding a claimant's eligibility for disability benefits. Appendices A, B, and C provide a non-exhaustive sample of key words, phrases, and/or symbols, respectively, which may be used by MRO application 130 to search the medical records. However, MRO application 130 may be configured to search for any common words used on standard hospital or doctor forms, commonly used words or phrases in the medical or disability industry, and terms provided by the user.

Consistent with various embodiments, numerous other criteria, other than key words, phrases, and symbols, may be employed by MRO application 130 to search through the medical records. For example, MRO application 130 may also search through the medical records to identify particular documents within the medical records. In this way, MRO application 130 may be configured to, for example, identify laboratory reports within the medical records.

Once computing device 400 has searched through the medical records and identified documents based on one or more criteria ("search results") in stage 220, method 200 may continue to stage 230 where computing device 400 may further process the search results to isolate and extract the DOI 120. For example, MRO application 130 may include functionality to isolate and extract the sentences, lines, or paragraphs in which the key words, phrases, and/or symbols are found. Furthermore, MRO application 130 may be configured to isolate and extract the paragraph(s) immediately following and/or preceding each of the key words, phrases, and/or symbols found in the documents.

For example, MRO application 130 may be configured to extract a pre-determined amount of data following or preceding an identified DOI 120. In this way, MRO application 130 may be configured to isolate full laboratory reports or partial laboratory reports (e.g., a single laboratory item, such as complete blood count (CBC), among multiple laboratory items in a laboratory report). Moreover, using a similar process, MRO application 130 may be configured to determine, for example, dates or category associated with the DOI. The detected date or category may then be tied to the isolated DOI for organizing the isolated DOIs in, for example, chronological or categorized order.

Accordingly, MRO application 130 may have the capability of identifying a pre-determined amount of data to isolate and include in a summary report 140 with each identified key word, phrase, or symbol. This may be accomplished using a combination of "positioning factors" used in isolating specific categories of key words, phrases, and symbols. The key words, phrases, and symbols may fall into a particular category based on the positioning factors as well as the intrinsic meaning of the specified key word, phrase, or symbol itself.

Interaction between the intrinsic meaning of a key word, phrase, or symbol and positioning factors may be better understood with reference to Appendix D, containing the phrase "History of present illness." The intrinsic meaning of this phrase may indicate that information immediately after it will provide historical data on an illness in question. Synonyms of the phrase may include the term 'subjective' or the symbol 'HPI'. Recognition of these key words, phrases, and symbols coupled with specific positioning factors may cause MRO application 130 to isolate a pre-determined amount of data associated with the recognized key words, phrases, and symbols for inclusion in the summary report 140.

Positioning factors may include, but not be limited to: a location where the key words, phrases, and symbols appear on a page, the presence of punctuation symbols such as colons, hyphens, or underlining, font size of characters in comparison with other data appearing on the page, and the presence (or absence) of data on the same line as the key words, phrases, and symbols.

In cases where, for example, key words, phrases, and symbols are used as headings, the position of the key words, phrases, and symbols on the page implies that it may represent a heading when it appears at the beginning of a line or shortly thereafter. The presence of associated punctuation symbols validates the context that the key words, phrases, and symbols are being used by strengthening the meaning of their use. For example, the presence of a colon symbol (:) after the phrase "history of present illness" implies that the subsequent data immediately following the phrase may be intensely associated with the phrase given the constructs of the English language.

In addition, a font size of the key words, phrases, and symbols may also provide valuable information. For example, in the context of key words, phrases, and symbols as headings, it may be often the case that the key words, phrases, and symbols are in a font size that is different (typically larger) than subsequent data on the same or succeeding lines. This circumstance may imply that the key words, phrases, and symbols are being used as a heading. Moreover, headings are often positioned on a line by themselves (i.e., no other characters or words or data is present on the line with the heading information). Accordingly, MRO application 130 may recognize key words, phrases, and symbols appearing on a page line with no (or few) other characters and determine its context as a heading.

Consistent with various embodiments, MRO application 130 may include functionality to isolate pristine text from disorganized text. For example, MRO application 130 may have searched through the medical records to identify text having a relatively high degree (e.g., 90% but this can be any chosen percentage) of recognition accuracy ("pristine text") and text having a relatively low degree (e.g., less than 90%) of recognition accuracy ("disorganized text"), for example, handwritten text. In turn, MRO application 130 may then isolate the pristine text from the disorganized text.

After computing device 400 isolated DOI from the medical records in stage 230, method 200 may proceed to stage 240 where computing device 400 may create/generate the summary report 140, containing the DOI 120 isolated and extracted from the searched medical records. For example, MRO application 130 may include functionality to allow the user to customize the order of the DOI 120 in the summary report 140 based on, for example, category of information or date. Summary report customization is discussed in greater detail below with respect to FIG. 3.

Consistent with various embodiments, numerous types of summary documents may be created. For example, as discussed above, MRO application 130 may include functionality to isolates full laboratory reports or partial laboratory reports. MRO application 130 may create the summary report 140 containing the content of the results of all electronically readable/searchable CBCs in the medical record categorized chronologically where possible.

Furthermore, and as discussed above, MRO application 130 may include functionality to isolate pristine text from disorganized text. Accordingly, MRO application 130 may create a summary document containing the disorganized text so that the user may review content containing sufficient handwritten text separately from the pristine text. Once computing device 400 has created the summary report 140 stage 240, the summary report 140 may be provided to a reviewing party through, for example, output device 150, or otherwise conveyed to a third party, and method 200 may then end at stage 250.

Consistent with various embodiments, MRO application 130 may include functionality to organize important dates and subject headings within the medical records. These important subject headings may include, for example, "History of Present Illness," "Hospital Course," "Admit Diagnosis," "Final Diagnosis," "Physical Examination," "Assessments," and "Laboratory Data." Headings may differ in various embodiments. For example, "physical examination" may be listed on a report as "PE" or "physical exam". In a manner similar to the method discussed with reference to FIG. 2, MRO application 130 may search the medical records to identify documents containing one or more of these headings or headings of similar import known in the industry and process the documents to isolate DOI and create summary report 140.

Appendix E illustrates one example of a summary report 140 based on searching the medical records of Appendix D for documents containing "History of Present Illness" headings and isolating DOI. In this example, the DOI is organized in chronological order. However, MRO application 130 may include functionality to allow a user to specify how the user would like the data presented (e.g., chronological or reverse chronological order).

Appendix F illustrates another example of a summary report 140 based on searching the medical records of Appendix D for documents containing the headings (1) "Diagnosis" "Assessment" or "Impression"; (2) Physical Examination; (3) "Hospital Course" or "Surgery" or headings of similar import. In this example, the DOI is organized in chronological order across all three categories of data. However, as will be discussed with referenced to FIG. 3, MRO application 130 may include functionality to allow a user to specify how the data for each category should be grouped together and presented.

Consistent with various embodiments, MRO application 130 may include functionality to capture relevant information related to the medical criteria for impairments listed in the Disability Evaluation under Social Security (DE/SS). For example, MRO application 130 may include functionality to allow a user to choose a specific category of impairments from a menu of options. Currently, DE/SS list for the following categories of impairments for adults: Musculoskeletal System; Special Senses and Speech; Respiratory System; Cardiovascular System; Digestive System; Genitourinary Impairments; Hematological Disorder; Skin Disorders; Endocrine System; Impairments that Affect Multiple Body Systems; Neurological; Mental Disorders; Malignant Neoplastic Diseases; and Immune System Disorders. MRO application 130 may include a menu having these listing of impairments for a user to choose. Once a specific category is selected, in a manner similar to the method disclosed with reference to FIG. 2, MRO application 130 may search the medical records for key words, phrases, and/or symbols associated with the medical criteria for the specific category. TABLE 1 lists a non-exhaustive list of key words, phrases, and/or symbols that may be used for the respiratory system.

TABLE 1

| Keywords | Phrases | Symbols |
| --- | --- | --- |
| asthma | pulmonary function test | CT chest |
| bronchiolitis | reactive airway disease | PFTS |
| pneumothorax | chronic asthma | RADS |
| wheezing | ventilator dependent | COPD |
| hemoptysis | oxygen desaturation | BAL |
| dyspnea | diffusing capacity | CXR |
| smoking | chest tomography | FEV1 |
| bronchodilator | arterial blood gas | FVC |
| pneumonia | lung cancer | DLCO |
| emphysema | sleep disorder | ABG |
| bronchitis | lung fibrosis | MVV |

TABLE 1-continued

| Keywords | Phrases | Symbols |
| --- | --- | --- |
| pneumoconiosis | chest x-ray | PO2 |
| spirometry | respiratory failure | PCO2 |
| antitrypsin | restrictive disease | ARDS |

MRO application 130 may then, in a manner similar to the method disclosed with reference to FIG. 2, further process the documents containing the key words, phrases, and/or symbols to isolate DOI and create the summary document 140. In this way, a substantial amount of time may be saved in analyzing the majority of medical records where the severity of the primary disease in question is measurable by objective testing (e.g., pulmonary function tests, echocardiography, and kidney function tests).

Still consistent with various embodiments, MRO application 130 may include functionality to allow a user to choose a specific disease from a menu of diseases (e.g., chronic illnesses). Once the specific disease is selected, in a manner similar to the method disclosed with reference to FIG. 2, MRO application 130 may search the medical records for key words, phrases, and/or symbols associated with complications of the disease. For example, if "diabetes mellitus" was selected from the menu of diseases, MRO application 130 may search the medical records to identify documents containing key words, phrases, and/or symbols associated with complications of diabetes such as "neuropathy", "acidosis", "retinopathy", and "NCS". TABLE 2 provides a list of diseases and a corresponding non-exhaustive list of key words, phrases, and/or symbols associated with the diseases.

TABLE 2

| Disease | Associated Key Words, Phrases, and/or Symbols |
| --- | --- |
| diabetes | "neuropathy", "diabetic retinopathy", "NCS" |
| hypertension | Cardiomyopathy, renal insufficiency, stroke, chronic renal failure (CRF) |
| chronic liver disease | Ascites, varices, encephalopathy |

Once MRO application 130 has searched the medical records, MRO application 130 may then, in a manner similar to the method disclosed with reference to FIG. 2, further process the documents containing the key words, phrases, and/or symbols to isolate DOI and create a summary document. By collecting specific data of interest that is known to act as objective factors in determining whether disability criteria are met and presenting this information in a summary report 140, MRO application 130 may allow for more efficient decision making by the medical records reviewer.

In various embodiments, MRO application 130 may include functionality to allow a user to choose a specific diagnosis from a menu of common second tier diagnoses. A second tier diagnosis may be a diagnosis that is commonly cited by disability claimants, but generally is not associated with a disabling impairment (i.e., a diagnosis without permanent impairment). The menu may be categorized by organ system. The following is a non-exhaustive list of second tier diagnosis that may be included in a menu for a user to choose: gastroesophageal reflux disease, irritable bowel syndrome, pancreatitis, atrial fibrillation, hepatitis, bradycardia, pulmonary edema, and syncope. Once the specific second tier diagnosis is selected, in a manner similar to the method disclosed with reference to FIG. 2, MRO application 130 may search the medical records for key words, phrases, and/or symbols associated with the diagnosis. For example, if "gastroesophageal reflux disease (GERD)" was selected from the menu of diagnosis, MRO application 130 may search the medical records to identify documents containing key words, phrases, and/or symbols associated with GERD such as "stricture", "Barrett's esophagus", and "EGD". TABLE 4 provides a list of common second tier diagnoses and a corresponding non-exhaustive list of associated key words, phrases, and/or symbols linked to the diagnoses.

TABLE 3

| Disease | Associated Key Words, Phrases, And/Or Symbols |
| --- | --- |
| emphysema | dyspnea, shortness of breath, PFT, CT chest, chest X-ray, bullae, smoking history |
| gastroesophgeal reflux dz | stricture, barretts esophagus, ulcer, EGD |
| mitral valve prolapse | palpitations, ECHO, leaflet, dyspnea, click |
| hepatitis | liver biopsy, immunotherapy, active hepatitis, cirrhosis |
| anemia | complete blood count, hemoglobin, bone marrow, CBC, HB |
| carpal tunnel syndrome | EMG/NCS, hypothenaratrophy, hand weakness |

Once MRO application 130 has searched the medical records, MRO application 130 may then, in a manner similar to the method disclosed with reference to FIG. 2, further process the documents containing the key words, phrases, and/or symbols to isolate DOI and create a summary document.

In addition to organizing the records by various subject areas, headings, key words, and phrases, embodiments may enable MRO application 130 to chronologically order the medical records. For example, MRO application 130 may employ search engines that are designed to identify dates that have been documented in the medical record in various forms. Dates in medical records may be typically represented by letters in combination with numeric characters. MRO application 130 may identify the representation of dates and organize DOI by date. In identifying the dates, MRO application 130 may include search functionality that has the capability to identify the differing representation of dates in the medical records. An example of some of the differing date representations can be expressed as follows: January 1, 2010; Jan 01, 2010; 01/01/10; Jan $1^{st}$ 2010; and 01-01-2010.

In various embodiments, MRO application 130 may convert the data representing a particular date to a common, uniform representation of the date for display as part of the summary report 140. In this way, MRO application 130 may display the requested medical record information linked to an associated date in a chronological fashion. For example, if a user requests a summary report 140 of the "History" and "Physical" (i.e., DOI associated with these two key words, phrases, and symbols) by date, the MRO application 130 will list identified DOI associated with the "History" and "Physical" with the dates sequenced to provide chronological order to the displayed data. MRO application 130 may also have the capability to reverse the chronological order of the displayed.

Consistent with embodiments, MRO application 130 may determine the date of each page in the medical record by either identifying the date on the page or associating the page with another page that has a date. Association may occur at the time a document is received by the MRO application 130 or thereafter. For example, if several pages are scanned or otherwise received into the MRO application 130 together, the MRO application 130 may associate the pages. As another example, an initial page may have headings "HPI" (i.e. History of Present Illness) and "Physical Exam". A second page would be expected to include headings such as "Lab Studies"

or "Assessment" or "Impression" or "Plan". MRO application 130 may search on these or similar headings and use their presence as a means of confirming that the second page is (very likely) associated with (i.e., is a continuation of) the aforementioned initial page (despite a missing same date as the initial page). As yet another example, MRO application 130 may verify page sequencing by identifying and matching type characteristics that are common within a set of medical records from an individual source. These type characteristics include, but are not limited to, the determination of font style, font size, and line spacing.

Moreover, embodiments may enable MRO application 130 to include the ability to compare page content (and/or data of interest) to eliminate duplications in the summary report 140. Because healthcare providers often transfer their treatment records among one another in the care of a patient, the collection of medical records from all available sources often creates duplication of some records (when all are sent to the reviewer from various medical sources). MRO application 130 may review and compare content to identify duplication and avoid including the duplication of DOI in the summary report 140.

In various embodiments, the functionality of MRO application 130 may include the ability to determine the most accurate date appearing on a page of medical record. Often a page of medical record may have several dates present. The functionality of MRO application 130 may use information appearing on the page containing multiple dates to identify which of the dates is most relevant (highest probability) to the date of actual service or date of record. The best date may be defined as a date which most accurately represents the 24-hour period that the medical activity in question actually occurred. MRO application 130 may be configured to identify a best date when three or fewer dates appear on a specific page where a DOI is present. MRO application 130 may employ several criteria known as qualifiers. The following phrases are non-limiting examples of qualifiers appearing in association with a date: 'date of exam'; 'date of service'; 'exam date'; discharge date'; and 'admission date'. MRO application 130 may be configured to locate these qualifiers and associated them with a best date when determining a date for the DOI 120.

In addition, MRO application 130 may also use a position of a date on a page as a qualifier. For example, dates appearing on a line with no additional text on the line may have a higher likelihood of being a best date than those dates appearing in the middle of a sentence located in the body of the page. In this way, MRO application 130 may include specific positioning criteria in determining a position qualifier in identifying the best date.

Consistent with embodiments, MRO application 130 may generate the summary report 140 that displays not only the best date, but other dates identified on a page containing the DOI 120. These additional dates will be displayed in order to enhance the awareness of the reviewer as these additional dates may have other significance in the review process.

Figure 3:
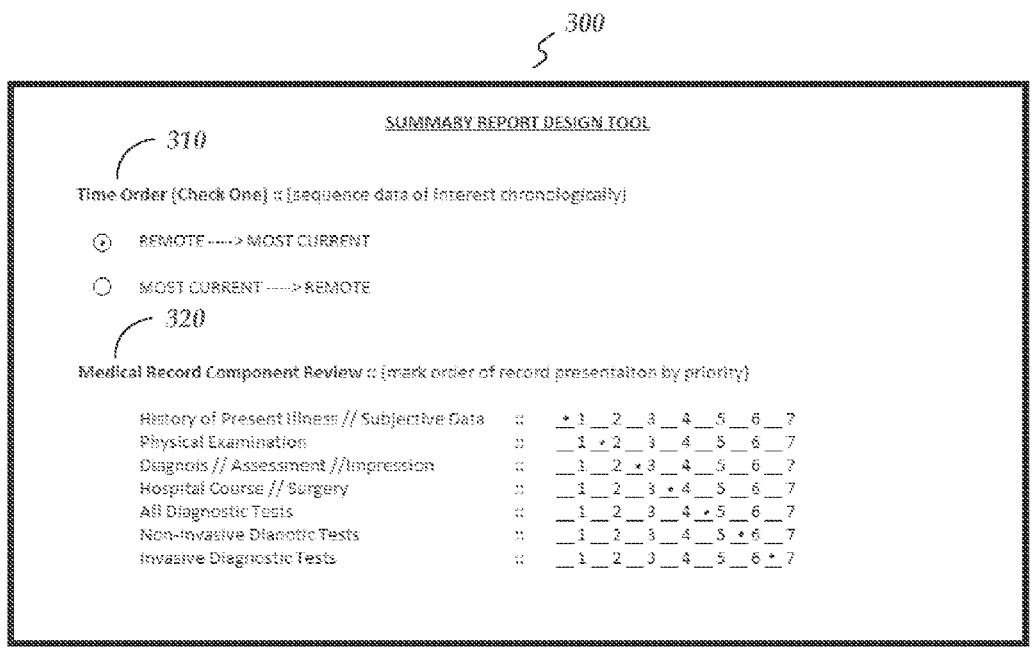
FIG. 3 is a diagram of an illustrative summary report design tool, in accordance with an embodiment.

FIG. 3 is one example of a summary report design tool 300 which may, in accordance with an embodiment, comprise a user interface generated by the MRO application 130 for display on a computing device. The summary report design tool 300 may include a Time Order section 310. This component of the application may allow the user to order the DOI 120 for enhancing the review process by providing chronological order to the DOI 120. It should be appreciated that presentation of the summary report in a chronological sequence may be useful to the reviewer in assessing important aspects of a claim. These aspects may include, without limitation, 1) disease course, 2) onset of complications, and 3) documentation of a date or dates of an actual diagnosis or diagnoses. Thus, the Time Order section 310 may enable a user of MRO application 130 to set a temporal order to the DOI 120 identified and presented by MRO application 130. In addition, the summary report design tool 300 may have a Medical Record Component Review section 320. The Medical Record Component Review section 320 may comprise a listing of various components for which the user of the MRO application 130 may set a presentation priority. By enabling the user of the MRO application 130 to set priorities to the components of the summary report 140, the user is permitted to customize the report to the user's individual preference or preferences. In particular, the components listed in the Medical Record Component review section 320 may represent several of the subject headings typically found in medical records and which are associated with the DOI 120. It should be understood that the subject headings shown in FIG. 3 are non-exhaustive and that additional components, such as an "Others" component may also be included for representing additional subject headings.

As discussed above, it should be appreciated that the MRO application 130 may order the presented DOI 120 according to one of or both time order and component order. It should be noted that the selection methods illustrated in FIG. 3 are for illustrative purposes and that other user interface selection methods may be provided for summary report design tool 300.

An embodiment may comprise a system for providing processing medical records. The system may comprise a memory storage and a processing unit coupled to the memory storage. The processing unit may be operative and configured to: convert a set of medical records into a computer-readable form; search the converted set of medical records to locate the DOI 120; extract the DOI 120 from the converted set of medical records; and generate the summary report 140 comprising the extracted DOI 120.

Another embodiment may comprise a system for processing medical records. The system may comprise a memory storage and a processing unit coupled to the memory storage. The processing unit may be operative and configured to: search a set of medical records to locate the DOI 120; identify the DOI 120 by: locating the searched at least one of the following: the keyword, the phrase, and the symbol, and designating an area surrounding the located at least one of the following: the keyword, the phrase, and the symbol as the DOI 120; extract the DOI 120 from the converted set of medical records; and generate the summary report 140 comprising the extracted DOI 120. Yet another embodiment may comprise a system for processing medical records. The system may comprise a memory storage and a processing unit coupled to the memory storage. The processing unit may operative and configured to: receive a set of medical records; convert the set of medical records into a computer-readable form; receive a search parameter associated with the DOI 120 within the set of medical records; search the medical records based on the search parameter; locate a portion of the medical records satisfying the search parameter; designate an area surrounding the portion of the medical records as the DOI 120; locate a representation of a date within the designated area; associate the date with the DOI 120; extract the DOI 120 from the from the medical records; generate the summary report 140 comprising the DOI 120 and the date associated with the DOI 120; and output the summary report 140.

Figure 4:
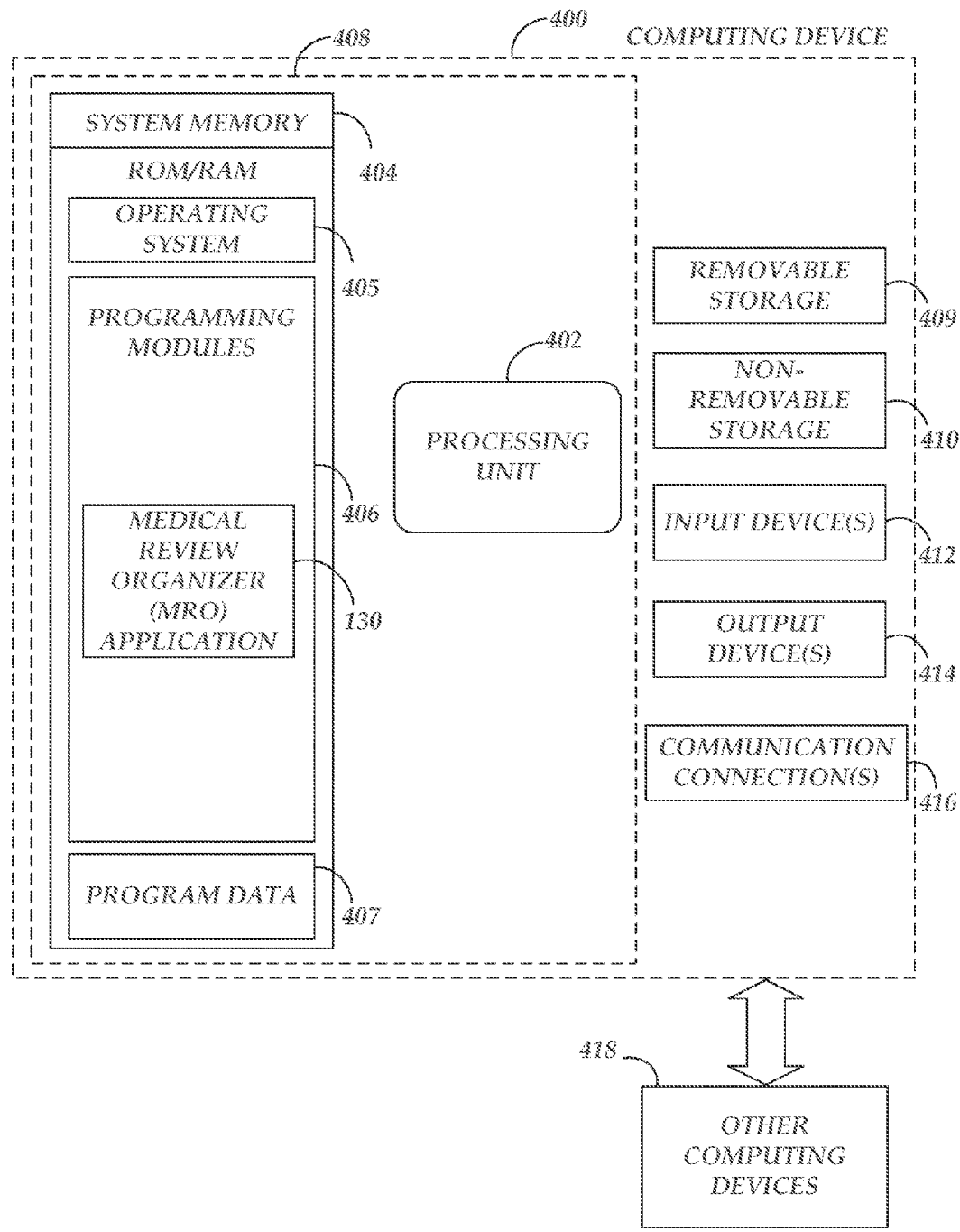
FIG. 4 is a block diagram of a system including a computing device for processing medical records, in accordance with various embodiments.

FIG. 4 is a block diagram of a system including computing device 400. Consistent with an embodiment, the aforementioned memory storage and processing unit may be implemented in a computing device, such as computing device 400 of FIG. 4. Any suitable combination of hardware, software, or firmware may be used to implement the memory storage and processing unit. For example, the memory storage and processing unit may be implemented with computing device 400 or any of other computing devices 418, in combination with computing device 400. The aforementioned system, device, and processors are examples and other systems, devices, and processors may comprise the aforementioned memory storage and processing unit, consistent with embodiments. Furthermore, computing device 400 may comprise an operating environment for system 100 as described above. System 100 may operate in other environments and is not limited to computing device 400.

With reference to FIG. 4, a system consistent with embodiments may include a computing device, such as computing device 400. In a basic configuration, computing device 400 may include at least one processing unit 402 and a system memory 404. Depending on the configuration and type of computing device, system memory 404 may comprise, but is not limited to, volatile (e.g. random access memory (RAM)), non-volatile (e.g. read-only memory (ROM)), flash memory, or any combination. System memory 404 may include operating system 405, one or more programming modules 406, and may include program data 407. Operating system 405, for example, may be suitable for controlling computing device 400's operation. In one embodiment, programming modules 406 may include a record reception module, a record conversion module, a record search module, a record extraction module, and a report generation module (not shown). It should be appreciated that the aforementioned modules may be embodied within a single programming module which may, in accordance with an embodiment, comprise the MRO application 130. Furthermore, embodiments may be practiced in conjunction with a graphics library, other operating systems, or any other application program and is not limited to any particular application or system. This basic configuration is illustrated in FIG. 4 by those components within a dashed line 408.

Computing device 400 may have additional features or functionality. For example, computing device 400 may also include additional data storage devices (removable and/or non-removable) such as, for example, magnetic disks, optical disks, or tape. Such additional storage is illustrated in FIG. 4 by a removable storage 409 and a non-removable storage 410. Computer storage media may include volatile and nonvolatile, removable and non-removable media implemented in any method or technology for storage of information, such as computer readable instructions, data structures, program modules, or other data. System memory 404, removable storage 409, and non-removable storage 410 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 400. Any such computer storage media may be part of device 400. Computing device 400 may also have input device(s) 412 such as a keyboard, a mouse, a pen, a sound input device, a touch input device, etc. Output device(s) 414 such as a display, speakers, a printer, etc. may also be included. The aforementioned devices are examples and others may be used.

Computing device 400 may also contain a communication connection 416 that may allow device 400 to communicate with other computing devices 418, such as over a network in a distributed computing environment, for example, an intranet or the Internet. Communication connection 416 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both storage media and communication media.

As stated above, a number of program modules and data files may be stored in system memory 404, including operating system 405. While executing on processing unit 402, programming modules 406 (e.g. the MRO application 130) may perform processes including, for example, one or more method 200's stages as described above. The aforementioned process is an example, and processing unit 402 may perform other processes. Other programming modules that may be used in accordance with various embodiments may include electronic mail and contacts applications, word processing applications, spreadsheet applications, database applications, slide presentation applications, drawing or computer-aided application programs, etc.

Generally, consistent with embodiments, program modules may include routines, programs, components, data structures, and other types of structures that may perform particular tasks or that may implement particular abstract data types. Moreover, embodiments may be practiced with other computer system configurations, including hand-held devices, multiprocessor systems, microprocessor-based or programmable consumer electronics, minicomputers, mainframe computers, and the like. Embodiments may also be practiced in distributed computing environments where tasks are performed by remote processing devices that are linked through a communications network. In a distributed computing environment, program modules may be located in both local and remote memory storage devices.

Furthermore, embodiments may be practiced in an electrical circuit comprising discrete electronic elements, packaged or integrated electronic chips containing logic gates, a circuit utilizing a microprocessor, or on a single chip containing electronic elements or microprocessors. Embodiments may also be practiced using other technologies capable of performing logical operations such as, for example, AND, OR, and NOT, including but not limited to mechanical, optical, fluidic, and quantum technologies. In addition, embodiments may be practiced within a general purpose computer or in any other circuits or systems.

Various embodiments, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the MRO application 130 may be embodied in hardware and/or in software (including firmware, resident software, micro-code, etc.). In other words, embodiments may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM).

FIG. 5 is a diagram of an illustrative summary report 140, in accordance with an embodiment. As discussed above, the summary report 140 may include the DOI 120 isolated and extracted from searched medical records (i.e., the medical record sources 110) organized by date. The summary report 140 may also include the page numbers 510 and 520 from the medical record sources 110 from which the DOI 120 (i.e., the content of the summary report 140) was extracted. For example, the DOI 120 bearing the date 4/20/05 in the summary report 140 was extracted from page 78 of the medical record sources 110 while the DOI 120 bearing the date 5/2/06 was extracted from page 225 of the medical record sources 120. It should be appreciated, that in accordance with an embodiment, the summary report 140 may be presented as a graphical user interface for display on a computer system and that the page numbers 510 and 520 may comprise hyperlinks (as shown by the underlining below the page numbers 78 and 225). In this embodiment, the hyperlinks may be utilized to take a user to the actual (digitized) medical record from which the DOI 120 was extracted from so that the user may conduct a more in-depth review of a patient's medical history. In accordance with an embodiment, the MRO application 130 may be configured to generate a display of the summary report 140 in a particular font style and font size selected by a user. Furthermore, in generating the summary report 140, the MRO application 130 may also be configured to convert from multiple different font styles and font sizes which may be associated with a single patient's medical history in the medical record sources 110, to the aforementioned user selected font style and/or font size. It should be also understood, that in accordance with an embodiment, the MRO application 130 may be configured to generate a display of the summary report 140 to include the DOI 120 between two dates specified by the user. It should be appreciated, by those skilled in the art, that insurance industry disability contracts are often structured to provide coverage during a specific time period. For example, there is a starting date of coverage (often referred to as the 'date insured' or 'date of insurance') and an end date which refers to the dated the coverage is discontinued. Medical conditions that were not present or diagnosed between these dates (depending on the specific language in the policy) would not be considered "covered" by the insurance policy (i.e., applicable to the policy). As a result, the insurance claim may be denied. Accordingly, as a convenience feature to the user, it should be appreciated that the ability to customize the summary report 130 to include the DOI 120 between specific dates may significantly enhance the efficiency of the review process.

Various embodiments, for example, are described above with reference to block diagrams and/or operational illustrations of methods, systems, and computer program products according to various embodiments. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments have been described, other embodiments may exist. Furthermore, although embodiments have been described as being associated with data stored in memory and other storage mediums, data can also be stored on or read from other types of computer-readable media, such as secondary storage devices, like hard disks, floppy disks, or a CD-ROM, a carrier wave from the Internet, or other forms of RAM or ROM. Further, the disclosed methods' stages may be modified in any manner, including by reordering stages and/or inserting or deleting stages, without departing from various embodiments.

All rights including copyrights in the code included herein are vested in and the property of the Applicant. The Applicant retains and reserves all rights in the code included herein, and grants permission to reproduce the material only in connection with reproduction of the granted patent and for no other purpose.

While the specification includes examples, the scope is indicated by the following claims. Furthermore, while the specification has been described in language specific to structural features and/or methodological acts, the claims are not limited to the features or acts described above. Rather, the specific features and acts described above are disclosed as example for various embodiments.

APPENDIX A

Listing of sample, non-exhaustive key words that may be used by MRO application 130 to search medical records.

Cardiovascular
Gastrointestinal
Back
Extremities
Musculoskeletal
Joints
Dexterity
Head
Ears
Eyes
Throat
Mouth
Gait
Pulmonary
Lung
Chest
Heart
Neck
Abdomen
Intestine
Artery
Vein
Muscle
Skin
X-ray
Tomography
Ultrasound
Electrocardiogram

APPENDIX A-continued

Listing of sample, non-exhaustive key words
that may be used by MRO application 130
to search medical records.

Electroencephalogram
Amputation
Medication
Pancreas
Arthritis
Hyperglycemia
Arm
Cardiomyopathy
Bone
Neuropathy
Impairment
Hernia
asthma
history
examination
meniscus
anemia
orthotic
tumor

APPENDIX B

Listing of sample, non-exhaustive phrases
that may be used by MRO application
130 to search medical records.

History of present illness
Chief complaint
Past medical history
Past surgical history
Review of systems
Hospital course
Discharge diagnosis
Procedures performed
Medication list
Physical examination
Social history
Exercise stress test
Operative report
Vital signs
Diagnostic impression
Lumbar spine
Cervical spine
Discharge summary
Chest X-ray
Substance abuse
Degenerative joint disease
Peripheral neuropathy
Diabetic neuropathy
Range of motion
Muscle atrophy
Disc herniation
Lumbar radiculopathy
Epidural steroid injection
Degenerative disc disease
Pain management
Nerve conduction studies
Joint deformity
Cervical fusion
Lumbar fusion
Spinal stimulator
Disc bulge
Congenital deformity
Cardic catheterization
Deep tendon reflexes
Permanent restriction
Maximal medical improvement
Activities of daily living
Congestive heart failure
Pulmonary function test
Airway obstruction
Magnetic resource imaging
Computed tomography

APPENDIX B-continued

Listing of sample, non-exhaustive phrases
that may be used by MRO application
130 to search medical records.

Ejection fraction
Antalgic gait
Assistive device

APPENDIX C

Listing of sample, non-exhaustive symbols
that may be used by MRO application
130 to search medical records.

COPD
ECG/EKG
EST
ECHO
PFT
CAD
CXR
CT
MRI
FEV1
FVC
GERD
EMG
NCS
IBS
IBD
LFT
NCV
U/S
UGI
XR
ESR
CBC
CMP
A1C
HCT
MUGA
SLR
HEENT
CVA
DOE
SOB
EGD
PSA
BMI
MSK
MMI
DJD
DDD
SVG
HPI
PE
ORIF
ROM
EF
HB
PLT
LAD
LVH
RCA

APPENDIX D

Sample Collection of Medical Records From Various
Sources.

Electronically signed by F. Murphy, M.D. on Nov. 13, 2008 at
12:20 a.m.
xxxx university Hospital
Discharge summary
Patient Name: Doe, John MRN: 0701259
Admit Date: Aug. 26, 2008
Discharge Date: Sep. 12, 2008
Problem List:
1. CHF
2. idiopathic dilated cardiomyopathy
3. Obesity
4. Renal insufficiency
5. anemia
Past medical history: hypertension, COPD, obesity.
Reason for admission: CHF exacerbation with cardiogenic shock
Final diagnosis: end-stage heartdz secondary to cardiomyopathy.
History of present illness: The patient is a 58 yr old male with end stage heart failure from nonischemic cardiomyopathy. His history begins one year ago when he received a chest x-ray which revealed cardiomegaly. He was diagnosed with dilated cardiomyopathy.
Hospital course:
He was referred to Dr. Nicolas Johnston and initially classified as a NYHA III. Mr. Doe was subsequently determined to require biventricular AICD placement because of left bundle branch block. Placement of defibrillator was performed on September $7^{th}$ without complication after this patient received optimal cardiac care with intropic agents and an after load reducing agent. During hospitalization renal insufficiency was noticed on day #3 with a creatonine of 2.2 subsequent fluid management resulted in an improvement with cr of 1.3 at time of discharge. Admission labs showed hemoglobin equal to 9.7 a work up for anemia revealed a low iron level and supplemental iron was initiated during hospital stay. The patient has been referred for GI consultation as an outpatient.
The patient continued to progress well after defibrillator placement. He was transferred from telemetry to a regular floor on September $10^{th}$. Diet was advanced to regular which was well to herated. Entry wound for defibrillator placement was observed to be clean without evidence of infection. Patient's ambulation was advanced after transfer to regular floor. He was deemed to be ready for discharge to home on Sep. 12, 2008.
Discharge medications:
Lisinopril
Aspirin
Pepcid
Ferrous Sulfate
1. Discharge instructions: The following extensive instructions were given to patient which included no heavy lifting, no driving, for 4 weeks. Continue low salt, low fat. Low cholesterol diet. The patient was asked to follow up on Sep. 28, 2008 with Dr. Hanson at xxxx university hospital (cardiology clinic) and Dr. Jeff George, a gastroenterologist, within the next 30 days.

Xxxx Hospital Echocardiogram Report

Patient: John Doe
Procedure date: Aug. 27, 2008
Referring physician: Frank Murphy, M.D.
SSN # xxxx-xx-0924
MRN: 07011259
Procedure: TTE
Indication: CHF
Measurements: (Normal in Parenthesis)
Estimated ejection fraction: 15 to 20% (55-75%)
Left Ventricular dimensions:
End diastole: 6.8 cm Septal wall: 0.9 cm (0.6-1.1)
End systole: 5.4 cm Posterior wall: 0.8 cm (0.6-1.1 cm)
Aorta: 2.6 cm (2.0-3.7 cm Left atrium: 4.2 (1.9-4.0)
Finding:
1. Technically adequate examination. Left ventricle is modestly dilated. Prominent trabeculation of lateral and inferior walls suggesting possible cardiomyopathy. LV ejection fraction is 15 to 20%. Overall left ventricular function appears severely reduced. The anteroseptal wall and the apex appear akinetic. All other walls appear severely hypokinetic.
Lung specialist of xxxx, p.c.
Patient: John Doe Date seen: Nov. 10, 2007
Acct #: 123-456 DOB: Jul. 1, 1950
Initial visit—progress note
Chief complaint: Shortness of breath with exertion.
HPI:
Mr. Doe is a 57 year old male who is here today due to increased shortness of breath with exertion. The patient reports becoming short of breath with yard work after a few minutes. He admits to history of cigarette smoking of 1 to 2 packs per day since the age of 20. Mr. Doe relates using over the counter inhaler (Primatene) which helps his symptoms somewhat. He does not recall having a chest Xray in the past five years.
Current medication:
Tylenol ES prn for back pain; norvasc 5 mg daily: OTC Primatene inhaler 2 puffs twice daily as needed.
Past medical history:
Hypertension (diagnosed 2002)
Low back pain (2006)
Past surgical history
Cholecystectomy (1995)
Colonoscopy with polyp removal (2000)
Social Hx:
Smoking 30+ years; social drinker once per month;
Denies illicit drug use
Review of systems:
HEENT: nasal congestion
Cardiovascular: exertional dyspnea
Respiratory: see HPI
Gastrointestinal: negative
Musculoskeletal: some mild degree of back discomfort
Neurological: negative
Physical examination:
BP: 130/70; temp: 99.2, pulse : 82 resp: 18
Ht: 6 feet 3 inches: wt 274 lbs
Appearance: tall, obese middle aged male in no acute distress.
Eyes: pupils are equal, round and reactive to light and accommodations
Neck: supple. No JVD
Respiratory: Bilateral expiratory wheezes throughout lung fields; no rales or rhonchi. No accessory muscle use. Cardiovascular: normal S1, S2. No murmurs or gallops. Gastrointestinal: protuberant abdomen, no organomegaly, non tender and without masses on deep palpation Musculoskeletal: grossly normal gait and station, no joint or extremity deformities, normal dexterity. Neurological: normal motor strength; no sensory deficits, intact deep tendon reflexes.
Assesment:
Probable COPD
Obesity
Tobacco dependency.
YYYY medical center
1068 Dover drive, sw
Chicago, IL 60616
Date: 13 Nov. 2007

Name: John Doe
Physician: G. Maddox, MD
Diagnosis: COPD
Chest, Two views
Clinical data: CHF
Findings: No previous similar study is available for comparison. The cardiac silhouette is moderately enlarged. Lung volume is symmetric without infiltrate or effusion. Pulmonary vascular is within normal limits. Lungs appear hyper expanded consistent with features of chronic obstructive pulmonary disease.
Dictated by: Kim G. Logan, M.D.
ZZZZ Family healthcare
Ohare office
275 Benjamin Blvd., Suite 130
Chicago, IL 60632
Patient: John Doe
Account #: 207195
Visit date: April 20, 2005
Subjective: Mr. Doe comes into the office complaining of persistant cough over the past 10 days. He reports production of green sputum on occasion for the last 3 days with episodes of fever and chills starting yesterday. He has no history of pneumonia, but is a smoker with a 25+ pack year history.
Objective: T=100.2, pulse =84, Resp=18, bp=144/82
HEENT: NC/AT, normal TMS, reactive pupils, clear posterior pharynx with no tonsillar plagues
Neck: supple, no cervical adenpatny
Lungs: coarse breath sounds, transient wheeze, no rales
Heart: regular rate and rhythm, no gallops or murmurs
ABD: Soft, nontender, active bowel sounds, no masses
Extremities—warm dry, no edema
Impression:
    1. Acute bronchitis
    2. elevated blood pressure
Plan:
    1. dextromethorphan 100 mg p.o. TID prn
    2. albuterol inhaler 2 puffs twice daily
    3. avoid smoking
    4. return in two weeks if symptoms persist
Xyz medical center
Emergency room report
Patient name: John Doe
DOB: Jul. 01, 1950
Encounter: 2100559
MRN: 0534006
Date of service: May 2, 2006
Time seen: 1250 hours
Chief complaint: lower back pain
History of present illness:
    This is a 55 year old male who presents with a one day history of back pain at the lower spine. He state that he lifted some equipment at work weighing approximately 70 lbs over a 10 minute period. The patient recalls experiencing sharp lower back pain near the end of the lifting. He denies any prior back injury. Pain has worsened over the past 24 hours and is described as throbbing with occasional "spasm like" sharp pain sensation. Denies change in bowel or bladder function. Also denies radiation of pain into hips or lower extremities. Taking Advil with no relief.
Past medical history: bronchitis; borderline hypertension
Past surgical history: none
Social history: smoker
Medication: Ibuprofen as needed
Allergies: none
Family history: noncontributory
Review of systems: All other systems reviewed were negative.
Physical examination: Patient is awake, alert, mildly distressed, and well developed. Temperature is 98.4 orally, blood pressure is 134/72; pulse 106, respirations 18, pulse ox is 98% on room air. HEENT exam was normal. Neck is supple with full range of motion. Chest is symmetrical. Lungs are clear bilaterally.
Heart: regular rate and rhythm.
Abdomen exam: nontender, no organomegaly, active bowel sounds.
Musculoskeletal: palpable spasm of lumbar paraspinous muscles; normal lordosis of T-L spine with good alignment; full room of all extremities. Neuro exam: 5/5 motor in all extremities, no sensory deficits grossly 2+ patella $DTR_s$. 1+ ankle $DTR_s$ bilaterally.
Clinical assessment: lumbar strain
Discharge medication: Darvocet N-100 one tab every 6 hours as needed for pain Disp # 10 cyclobenzaprine 10 mg one twice daily Disp: # 10
Condition at discharge: stable
Xyz medical center
Radiology department
Patient name: John, Doe
DOB: Jul. 01, 1950
Encounter: 2100562
MRN: 0534006
Date of service: May 2, 2006
Time See: 1410 hours
Ordering Physician: James Howard
Diagnosis: low back pain
Lumbar spine series
Findings:
    Views of the lumber spine show the 5 lumbar vertebrae to be in normal anatomic alignment. This is uniform vertebral body height present. No evidence of acute fractures is identified. Minimal disc space narrowing is noted at L5-S1.
Impression: No evidence of acute osseous abnormality.
Signed: Andrea B. Jenkins, MD
ABC Orthopedic clinic
705 Pinnacle Blvd. Ste 600
Springfield, IL 62708
Name: John Doe
Acct #: 186020
Exam date: Dec. 15, 2009
Subjective: Mr. Doe is being evaluated for a complaint of chronic low back pain. He recalls a work related injury in 2006 involving his back. He states his symptoms resolved after a few weeks, but his current pain feels the same. Mr. Doe reports his low back pain (LBP) is located in the same area with occasional radiation into the hips. No bladder or bowel changes.
Family History: Osteoporosis in sister.
Social History: + smoking; rare alcohol use.
Work history: Warehouse worker ×12years includes forklift operation and occasional lifting 50 lbs.
Current medications: Norvasc (BP control)
Ibuprofen (takes 4 200 mg tabs)
PE: Lungs: clear
Heart: regular rate, rhythm; no murmurs
Musculoskeletal—normal curvature of L spine
Unable to heel toe walk; flexion of lumbar spine is 20 degrees and limited by pain; extension is 10 degrees with pain; straight leg raises are equivocal at 20 degrees. Full ROM at hips without pain. No leg length discrepancy or hip flexion contracture.

Neurological—motor function with normal 5/5 responses in LE's except right foot/leg; 3/5 motor of right leg/foot diffusely. Normal sensory exam to light touch and pin prick in lower extremities except decrease sensation on dorsum of right foot. Equal and symmetric reflexes at knees and ankles No clonus Diagnosis:

Lumbar Radiculopathy

Plan: Order:
1. Lspine MRI
2. Percocet 5-32s one by mouth every 6 hrs prn
3. work restriction—no lifting 10 lbs until next office visit.

Doctor's hospital of xxxx

Check in # 725606

Exam 1219

Desc MRI Lumbar

Ord. Diag.

Radiculopathy

Indication: Back pain, right LE numbness

Technique: Sagittal; T1. proton density and were obtained to the lumbar spine, followed by axial oblique proton density and T2 weighted imaging through the lower three lumbar interspaces.

Findings:

Normal lumbar alignment. No fractures, subluxation, or focal osseous lesions are demonstrated. There is disc space narrowing with dessication at L4-L5. Unremarkable conus.

Mild bulging annulus at L4-L5 and L5-S1. Slight flattening of the ventral theal sac at these levels. No specific nerve root compression seen. No suggestion of neural foraminal or lateral root impingement at these levels. Small inferior neural foraminal narrowing a L5-S1 without evidence of impingement.

Read by: Jason Mcwhorter, MD

Date time released: Dec. 16, 2009 1620

Name: John Doe

Date of Birth: Jul. 1, 1950

Date of Exam: Mar. 22, 2010

INDEPENDENT MEDICAL EXAMINATION

Patient Profile:

Mr. Doe is a 59 year old gentleman who presents at the request of the City of XXX for an independent medical examination. He is employed with ZZZ School System as a warehouseman and is being assessed for both work & non-work-related medical condition(s).

Sources of Information:
1. History from Mr. Doe
2. Medical records from Dr. F. Murphy of xxx University Hospital
3. Medical records from Dr. Jason McWhorter at Doctors Hospital of XXX History of Present Illness:

Mr. Doe relates that some time in 2007 he received a chest X-ray as part of screening process prior to participation in a weight loss program. He was told that his heart showed signs of enlargement. Subsequent testing led to a diagnosis of dilated cardiomyopathy.

In August 2008 Mr. Doe recalls being hospitalized at xxx University Hospital with a primary diagnosis of congestive heart failure. He was treated and received an automatic intracardiac defibrillator while there. Mr. Doe reports feeling generalized fatigue several days each week, but denies any recent episodes of chest pain, shortness of breath, or lower extremity edema. He reports being able to walk approximately 5 blocks before requiring a rest break.

Mr. Doe recalls that in 2006 he was lifting equipment while at work when he felt a sharp pain in his lower back. He specifically recalls that he was moving equipment at the warehouse where he is employed. Mr. Doe relates that he was evaluated at an emergency room and told that he had a back strain. He remarks that his back initially improved but that over the past 4 months he has experienced the same sort of back pain in the exact same area of his spine. Mr. Doe indicates that he was evaluated in December of 2009 by an orthopedic specialist in Springfield. He does not remember the name of the doctor, but reports that he received an MRI of his back afterward. He does not know the results of the MRI.

Mr. Doe states that he experiences a chronic cough that comes and goes. He admits that the cough is typically dry with occasional phlegm production. He denies associated fever, chills, or sore throat. Mr. Doe remarks that he is a long-term smoker with a pack-a-day habit since his late teenage years. He states that his ability to participate in any strenuous activity has been limited by shortness of breath in the past year or so. Mr. Doe states that he occasionally becomes winded (short of breath) at work with increasing work activities. He remarks that he has been unsuccessful at stopping smoking though he has made several attempts.

With daily activities Mr. Doe indicates that the back pain bothers him more at night. He remarks that he generally only gets 4 or 5 hours of sleep at night. He relates having difficulty putting his underwear on and tying his shoes. He admits some limited relief with exercises introduced in physical therapy. He states he can only drive for approximately 1 hour because he must stop to stretch. Mr. Doe estimates he can stand in his kitchen for 30 minutes only; standing for longer a period leads to backache. He report having several walking canes, but denies using a cane at work for fear of job loss.

Allergies:

None.

Current Medications:

Ibuprofen 800 mg one tab twice daily

Darvocet one tab as needed

Nexium one tab as needed

Past Medical History:

Hypertension [borderline] (2006)

Bronchitis (2005)

Congestive heart failure (2008)

Low back pain (2006)

Social History:

Married with 1 children (age 37)); smoker—smoked approx. 1 pack per week for 30+ years; occasional social use of wine only; denies illicit drug use; educational level—high school graduate.

Review of Systems:

Neurological: pain radiation from back into hips/thighs

Respiratory: dyspnea with exertion; cough

Cardiovascular: non-contributory

Gastrointestinal: heartburn

Musculoskeletal: low back pain;

Skin: non-contributory

Occupational History/Duties:

Mr. Doe recalls that he began his work with the City of XXXX 1993. He states that his job title then was warehouseman and has remained in this position. Duties involve maintaining school equipment inventory to supply various schools throughout the system. Duties include loading/unloading furniture, and use of forklifts, and carriage equipment.

Physical Examination:
General: well-developed, well-nourished tall black male seen rising slowly from his chair in waiting area and walking steadily with normal slowed gait with no use of an assistive device in no acute distress
Vital Signs: T: 97.3; BP: 140/86; P: 76; R: 12; Ht: 75 in.; Wt.: 288 lbs.
HEENT:
Normocephalic, atraumatic; tympanic membranes intact bilaterally; extraocular muscles intact; right eyelid lag noted; pupils—equal and reactive to light, arcus senilus noted; fundi—benign; nose—large nasal polyps present in both nostrils; fair dentition with upper dental appliance, posterior pharynx clear
Neck:
Supple, no thyromegaly, no cervical adenopathy, no jugular venous distension
Pulmonary/Chest:
Clear to auscultation; normal breath excursions with decreased breath sounds; subtle evidence of pectus excatavum at anterior chest wall
Heart:
Regular rate and rhythm without gallop or murmur
Abdomen:
Soft, nontender, active bowel sounds, no organomegaly, no bruits
Extremities:
Warm, dry, no edema, 1+ posterior tibialis pulses
Back:
Normal spinal curvature, no evidence of scoliosis or kyphosis; straight leg raises (supine) to 40 deg on right and 50 deg on left; supine hip flexion to 85 deg on right and 90 deg on left; forward flexion to 20 deg; extension to 5 deg; left lateral bend to 10 deg; right lateral bend to 10 deg; left rotation to 25 deg, right lateral rotation to 15 deg;
Neurological:
Alert, oriented to person, place, time, and situation; 5/5 grip strength bilaterally; 5/5 power of upper extremities in flexion and extension at elbow joints bilaterally; 5/5 power of lower extremities in flexion and extension at knee joints bilaterally; slightly slowed otherwise normal gait; Romberg test—negative; no heel walking able to stand in one place on heels; unable to stand or walk on toes
Pertinent Laboratory Studies:
Pulmonary Function Tests (performed at office today)—FEV1=2.2 liters, FVC =2.65 (good effort given)
Clinical Impression:
1. Lumbar degenerative disc disease
2. Chronic obstructive pulmonary disease
3. History of congestive heart failure (CHF)
4. History of hypertension
Medical Statement:
Examinee is able to walk and stand normally. MRI findings (from review of medical records) and PE results are consistent with a moderate restriction on lifting/carrying with recommended occasional lifting of 20 lbs and frequently lifting/carrying of 10 lbs. He should be able to stand/walk at least 6 hours per work day with normal, routine breaks as well as sit for 6 to 8 hours. Examinee is able to reach, handle, and feel his fingers on hands. He is able to climb, balance, stoop, and bend with mild/moderate restriction. The examination did not identify any limitations with respect to intolerances to heat, cold, fumes, dust, or noise. The examinee hears, sees, and speaks in a normal fashion.

Brian X. Colson, M.D.
Date of examination: Mar. 3, 22, 2010

APPENDIX E

Summary Report # 1
History of Present Illness//Subjective Data
Apr. 20, 2005
Subjective: Mr. Doe comes to the office complaining of persistent cough over past 10 days. He reports production of green sputum on occasion for last 3 days with episodes of fever and chills starting yesterday. He has no history of pneumonia but is a smoker with a 25+ pack year history.
May 2, 2006
History of Present Illness:
This is a 55 year-old male who presents with a one day history of back pain at the lower spine. He sates that he lifted some equipment at work weighing approximately 70 lbs over a 10 minute period. The patient recalls experiencing . . .
Nov. 10, 2007
HPI:
Mr. Doe is a 57 year-old gentleman who is here today due to increased shortness of breath with exertion. The patient reports becoming short of breath with yard work after a few minutes. He admits to history of cigarette smoking 1 to 2 packs per ay since age 20. Mr. Doe relates using . . .
Sep. 12, 2008
History of Present Illness: The patient is a 58 year old male with end stage heart failure from non-ischemic cardiomyopathy>his history begins one year ago when he received a chest X-ray which revealed cardiomegaly. He was diagnosed with dilated cardiomyopathy.
Dec. 5, 2009
Subjective: Mr. Doe is being evaluated for a complaint of chronic low back pain. He recalls a work-related injury in 2006 involving his back He states his symptoms resolved after a few weeks, but his current pain feels the same. Mr. Doe reports his low back pain (LBP) is located in the same area with occasional radiation into hips. No bladder or bowel changes.
Mar. 22, 2010
History of Present Illness:
Mr. Doe relates that some time in 2007 he received a chest X-ray as part of screening process prior to participation in a weight loss program. He was told that his heart showed signs of enlargement. Subsequent testing led to a diagnosis of dilated cardiomyopathy.
In August 2008 Mr. Doe recalls being hospitalized at xxx University Hospital with a primary diagnosis of congestive heart failure. He was treated and received an automatic intraccardiac defibrillator while there. Mr. Doe reports feeling generalized fatigue several days each week, but denies any recent episodes of chest pain,shortness of breath, or lower extremity edema.. He reports being able to walk approximately 5 blocks before requiring a rest break.
Mr. Doe recalls that in 2006 he was lifting equipment while at work when he felt a sharp pain in his lower back. He specifically recalls that he was moving equipment at the warehouse where he is employed. Mr. Doe relates that he was evaluated at an emergency room and told that he had a back strain. He remarks that his back initially improved but that over the past 4 months he has experienced the same sort of back pain in the exact same area of his spine. Mr. Doe indicates that he was evaluated in December of 2009 by an orthopedic specialist in Springfield. He does not remember the name of the doctor, but reports that he received an MRI of his back afterward. He does not know the results of the MRI.
Mr. Doe states that he experiences a chronic cough that comes and goes. He admits that the cough is typically dry with occasional phlegm production. He denies associated fever, chills, or sore throat. Mr. Doe remarks that he is a long-term smoker with a pack-a-day habit since his late teenage years. He states that his ability to participate in any strenuous activity has been limited by shortness of breath in the past year or so. Mr. Doe states that he occasionally becomes winded (short of breath) at work with increasing work activities. He remarks that he has been unsuccessful at stopping smoking though he has made several attempts.

With daily activities Mr. Doe indicates that the back pain bothers him more at night. He remarks that he generally only gets 4 or 5 hours of sleep at night. He relates having difficulty putting his underwear on and tying his shoes. He admits some limited relief with exercises introduced in physical therapy. He states he can only drive for approximately 1 hour because he must stop to stretch. Mr. Doe estimates he can stand in his kitchen for 30 minutes only; standing for longer a period leads to backache. He report having several walking canes, but denies using a cane at work for fear of job loss.

APPENDIX F

Summary Report # 2
(1)"Diagnosis" "Assessment" or "Impression"; (2) Physical Examination; (3) "Hospital Course" or "Surgery"
Apr. 20, 2005
Impression:
 1. Acute bronchitis
 2. elevated blood pressure
May 2, 2006
Clinical assessment: lumbar strain
Impression: No evidence of acute osseous abnormality
Nov. 10, 2007
Assesment:
Probable COPD
Obesity
Tobacco dependency.
Physical examination:
BP: 130/70; temp: 99.2, pulse : 82 resp: 18
Ht: 6 feet 3 inches: wt 274 lbs
Appearance: tall, obese middle aged male in no acute distress.
Eyes: pupilsare equal, round and reactive to light and accommodations
Neck: supple. No JVD
Respiratory: Bilateral expiratory wheezes throughout lung fields; no rales or rhonchi. No accessory muscle use. Cardiovascular: normal s, sz. No murmers or gallops. Gastrointestinal: protuberant abdomen, no, organomegaly, non tender and without masses on deep palation musculoskeletal: grossly normal gait and station, no joint or extremity deformities, normal dexterity. Neurological: normal motor strength; no sensory deficits, intact deep tendon reflexes
Nov. 13, 2007
Diagnosis: COPD
Aug. 26, 2008
Final diagnosis: end-stage heartdz secondary to cardiomyopathy.
Hospital course:
 He was referred to Dr. Nicolas Johnston and initially classified as a NYHA III. Mr, Doe was subsequently determined to require biventricular AICD placement because of left bundle branch block. Placement of defibrillator was performed on Sep. 7 without complication after this patient received optimal cardiac care with intorpic agents and an after load reducing agent. During hospitalization renal insufficiency was noticed on day #3 with a creatonine of 2.2 subsequent fluid management resulted in an improvement with cr of 1.3 at time of discharge. Admission labs showed hemoglobin equal to 9.7 a work up for anemia revealed a low iron level and supplemental iron was initiated during hospital stay. The patient has been referred for 61 consultation as an outpatient.

The patient continued to progress well after defibrillator placement. He was transferred from tememetry to a regular floor on Sep. 10. Diet was advanced to regular which was well to herated. Entry wound for defibrillator placement was observed to be clean without evidence of infection. Patient's ambulation was advanced after transfer to regular floor. He was deemed to be ready for discharge to home on Sep. 12, 2008.
Dec. 5, 2009
Diagnosis:
Lumbar Radiculopathy
PE: Lungs: clear
Heart: regular rate, rhythm; no murmers
Musculoskeletal—normal curvature of 1 spine
 Unable to heel toe walk; flexion of lumber spine is 20 degrees and limited by pain; extension is 10 degrees with pain; straight leg raises are equivocal at 20 degrees. Full ROM at hips without pain. NO leg length discrepancy or hip flexion contracture.
Neurological—motor function with normal 5/5 responses in LE's except right foot/ leg; 3/5 motor of right leg/foot diffusely. Normal sensory exam to light touch and pin prick in lower extremities except decrease sensation on dorsum of right foot. Equal and symmetric reflexes at knees and ankles. No clonus
Mar. 22, 2010
Clinical Impression:
 1. Lumbar degenerative disc disease
 2. Chronic obstructive pulmonary disease
 3. History of congestive heart failure (CHF)
 4. History of hypertension
Physical Examination:
General: well-developed, well-nourished tall black male seen rising slowly from his chair in waiting area and walking steadily with normal slowed gait with no use of an assistive device in no acute distress
Vital Signs: T: 97.3; BP: 140/86; P: 76; R: 12; Ht: 75 in.; Wt.: 288 lbs.
HEENT:
 Normocephalic, atraumatic; tympanic membranes intact bilaterally; extraocular muscles intact; right eyelid lag noted; pupils—equal and reactive to light, arcus senilus noted; fundi—benign; nose—large nasal polyps present in both nostrils; fair dentition with upper dental appliance, posterior pharynx clear
Neck:
Supple, no thyromegaly, no cervical adenopathy, no jugular venous distension
Pulmonary/Chest:
Clear to auscultation; normal breath excursions with decreased breath sounds; subtle evidence of pectus excatavum at anterior chest wall
Heart:
Regular rate and rhythm without gallop or murmur
Abdomen:
Soft, nontender, active bowel sounds, no organomegaly, no bruits
Extremities: Warm, dry, no edema, 1+ posterior tibialis pulses
Back:
 Normal spinal curvature, no evidence of scoliosis or kyphosis; straight leg raises (supine) to 40 deg on right and 50 deg on left; supine hip flexion to 85 deg on right and 90 deg on left; forward flexion to 20 deg; extension to 5 deg; left lateral bend to 10 deg; right lateral bend to 10 deg; left rotation to 25 deg, right lateral rotation to 15 deg;

Neurological:

Alert, oriented to person, place, time, and situation; 5/5 grip strength bilaterally; 5/5 power of upper extremities in flexion and extension at elbow joints bilaterally; 5/5 power of lower extremities in flexion and extension at knee joints bilaterally; slightly slowed otherwise normal gait; Romberg test—negative; no heel walking able to stand in one place on heels; unable to stand or walk on toes

What is claimed is:

1. A method for processing medical records, the method comprising:
   receiving, by a computer, a set of medical records stored in a database, the set of medical records stored in the database being linked to a claimant and comprising data of interest (DOI), the DOI comprising one or more of key words, phrases and symbols related to medical criteria for impairments, the set of medical records and further comprising a plurality of qualifiers, each of the plurality of qualifiers comprising a phrase associated with a date and a position of the date on a page in the set of medical records, the dates associated with the plurality of qualifiers being represented in a non-uniform fashion in the set of medical records, wherein the position of the date on the page in the set of medical records comprises a date appearing on a line of text on the page having no additional text on the line;
   determining that the date appearing on the line of text on the page having no additional text on the line has a higher likelihood of being a best date than dates appearing in the middle of a sentence located in a body of the page;
   converting, by the computer, the set of received medical records into a computer-readable form;
   searching, by the computer, the converted set of medical records to locate the DOI and the plurality of qualifiers;
   determining, by the computer, the dates associated with the DOI based on the plurality of qualifiers;
   extracting, by the computer, the DOI from the converted set of medical records; generating, by the computer, a summary report comprising the extracted DOI; and
   customizing, by the computer, the summary report, wherein customizing the summary report comprises:
   converting the dates associated with the DOI to a common and uniform date representation for display;
   receiving a user selection of a chronological order of DOI presentation in a graphical user interface displayed by the computer; and
   in response to receiving the user selection, organizing the summary report such that the DOI is presented in the chronological order by the dates associated with the DOI.

2. The method of claim 1, wherein searching the converted set of medical records comprises identifying the one or more of key words, phrases and symbols.

3. The method of claim 2, wherein identifying at least one of the following: the keyword, the phrase, and the symbol comprises receiving a user specification of the one or more of key words, phrases and symbols.

4. The method of claim 1, wherein searching the converted set of medical records comprises identifying documents within the converted set of medical records.

5. The method of claim 4, wherein identifying the documents within the converted set of medical records comprises identifying a laboratory report, and wherein extracting the DOI comprises extracting one of the following: a portion of the laboratory report and the entire laboratory report.

6. The method of claim 1, wherein extracting the DOI comprises extracting an area of a page within the set of medical records, the area of the page surrounding a search term associated with the DOI.

7. The method of claim 6, wherein extracting the area of the page within the set of medical records comprises extracting a predetermined amount of data from the page, the predetermined amount of data being based on a proximity of a search term associated with the DOI to at least one of the following: a header, a beginning of a sentence, an end of a sentence, a beginning of a paragraph, an end of a paragraph, and a punctuation mark.

8. The method of claim 1, further comprising outputting the summary report, wherein outputting the summary report comprises at least one of the following:
   providing the summary report to a storage device,
   providing the summary report to a display device,
   providing the summary report to a printing device, and
   electronically communicating the summary report over a network.

9. The method of claim 1, wherein searching the converted set of medical records comprises identifying at least one heading.

10. The method of claim 1, wherein determining, by the computer, the dates associated with the DOI based on the plurality of qualifiers comprises determining a best date for the DOI when the set of medical records provides more than one date in proximity to the DOI, wherein the best date comprises a date which most accurately represents a twenty-four hour period during which a particular medical activity associated with the set of medical records occurred.

11. The method of claim 1, wherein the plurality of qualifiers comprises one or more of the following phrases: date of exam, date of service, exam date, discharge date and admission date.

12. A non-transitory computer-readable storage device comprising a set of instructions which when executed by a computer perform a method of processing medical records, the method executed by the set of instructions comprising:
   receiving a set of medical records stored in a database, the set of medical records stored in the database being linked to a claimant and comprising data of interest (DOI), the DOI comprising one or more of key words, phrases and symbols related to medical criteria for impairments, the set of medical records and further comprising a plurality of qualifiers, each of the plurality of qualifiers comprising a phrase associated with a date and a position of the date on a page in the set of medical records, the dates associated with the plurality of qualifiers being represented in a non-uniform fashion in the set of medical records, wherein the position of the date on the page in the set of medical records comprises a date appearing on a line of text on the page having no additional text on the line;
   determining that the date appearing on the line of text on the page having no additional text on the line has a higher likelihood of being a best date than dates appearing in the middle of a sentence located in a body of the page;
   receiving a user specification of the one or more of key words, phrases and symbols;
   converting the set of received medical records into a computer-readable form;
   searching the converted set of medical records to locate the DOI and the plurality of qualifiers data of interest (DOI);
   determining the dates associated with the DOI based on the plurality of qualifiers;

extracting the DOI from the converted set of medical records;
generating a summary report comprising the extracted DOI; and
customizing the summary report, wherein customizing the summary report comprises:
  converting the dates associated with the DOI to a common and uniform date representation for display;
  receiving a user selection of a chronological order of DOI presentation in a graphical user interface displayed by the computer; and
  in response to receiving the user selection, organizing the summary report such that the DOI is presented in the chronological order by the dates associated with the DOI.

13. The non-transitory computer-readable storage device of claim 12, wherein extracting the DOI comprises extracting an area of a page within the set of medical records, the area of the page surrounding a search term associated with the DOI, wherein extracting the area of the page within the set of medical records comprises extracting a predetermined amount of data from the page, the predetermined amount of data being based on a proximity of a search term associated with the DOI to at least one of the following: a header, a beginning of a sentence, an end of a sentence, a beginning of a paragraph, an end of a paragraph, and a punctuation mark.

14. The non-transitory computer-readable storage device of claim 12, wherein determining the dates associated with the DOI based on the plurality of qualifiers comprises determining a best date for the DOI when the set of medical records provides more than one date in proximity to the DOI, wherein the best date comprises a date which most accurately represents a twenty-four hour period during which a particular medical activity associated with the set of medical records occurred.

15. The non-transitory computer-readable storage device of claim 12, wherein the plurality of qualifiers comprises one or more of the following phrases: date of exam, date of service, exam date, discharge date and admission date.

16. A system for processing medical records, the system comprising:
a memory storage, and
a hardware processing unit coupled to the memory storage, the processing unit being configured to:
  receive a set of medical records stored in a database, the set of medical records stored in the database being linked to a claimant and comprising data of interest (DOI), the DOI comprising one or more of key words, phrases and symbols related to medical criteria for impairments utilized for a disability evaluation, the set of medical records and further comprising a plurality of qualifiers, each of the plurality of qualifiers comprising a phrase associated with a date and a position of the date on a page in the set of medical records, the dates associated with the plurality of qualifiers being represented in a non-uniform fashion in the set of medical records;
  convert the set of received medical records into a computer-readable form;
  search the converted set of medical records to locate the DOI and the plurality of qualifiers;
  determine the dates associated with the DOI based on the plurality of qualifiers, wherein determining the dates associated with the DOI based on the plurality of qualifiers comprises determining a best date for the DOI when the set of medical records provides more than one date in proximity to the DOI, wherein the best date comprises a date which most accurately represents a twenty-four hour period during which a particular medical activity associated with the set of medical records occurred, wherein the plurality of qualifiers comprises one or more of the following phrases: date of exam, date of service, exam date, discharge date and admission date, wherein the position of the date on a page in the set of medical records comprises a date appearing on a line of text on the page having no additional text on the line;
  determine that the date appearing on the line of text on the page having no additional text on the line has a higher likelihood of being the best date than dates appearing in the middle of a sentence located in a body of the page;
  extract the DOI from the converted set of medical records;
  generate a summary report comprising the extracted DOI;
  customize the summary report, wherein customizing the summary report comprises:
    converting the dates associated with the DOI to a common and uniform date representation for display;
    receiving a user selection of a chronological order of DOI presentation in a graphical user interface displayed by the computer; and
    in response to receiving the user selection, organizing the summary report such that the DOI is presented in the chronological order by the dates associated with the DOI; and output the summary report.

* * * * *